US00PP11000P

United States Patent [19]

Brown et al.

[11] Patent Number: Plant 11,000

[45] **Date of Patent: *Jul. 6, 1999**

[54] APPLE CULTIVAR 'FORTUNE'

[75] Inventors: Susan K. Brown, Geneva; Roger D. Way, Stanley; David E. Terry, Ovid; Kenneth G. Livermore, Geneva, all of N.Y.

[73] Assignee: Cornell Research Foundation, Inc., Ithaca, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/831,761

[22] Filed: Apr. 1, 1997

Related U.S. Application Data

[63] Continuation of application No. 08/629,792, Apr. 9, 1996, abandoned, which is a continuation of application No. 08/401,837, Mar. 10, 1995, abandoned.

[51] Int. Cl.[6] ..... A01H 5/00

[52] U.S. Cl. ..... Plt./161

[58] Field of Search ..... Plt./34.1, 161, Plt./174

[56] References Cited

PUBLICATIONS

Holloway, P.J. (1982) "Suberins of *Malus pumila* Stem and Root Corks", *Phytochemistry* vol. 21, No. 10 pp. 2517–2522.

*Primary Examiner*—Howard J. Locker

[57] ABSTRACT

A new distinctive cultivar of apple (*Malus Xdomestica*) which is exceptional in combining the desirable appearance of 'Empire' with much larger fruit size, and the processing quality of 'Northern Spy' without the production problems of 'Northern Spy'. It offers growers and consumers a large attractive fruit that can be used fresh or for cooking. The cultivar is named 'Fortune' and was tested as NY 429.

4 Drawing Sheets

CROSS-REFERENCE TO RELATED APPLICATIONS

This application is a continuation of Plant Application Ser. No. 08/629,792, filed Apr. 9, 1996, now abandoned, which is a continuation of Plant Application Ser. No. 08/401,837, filed Mar. 10, 1995, now abandoned.

BACKGROUND OF THE INVENTION

In 1962 hybrid seeds were created from controlled pollinations between 'Schoharie Spy' (a sport of 'Northern Spy') and 'Empire'. A population of 542 seedlings with the New York State Agricultural Experiment Station progeny designation 62621 were planted June of 1964 on the Sullivan Farm of the Cornell University's New York State Agricultural Experiment Station at Geneva, N.Y. One seedling in this population was planted in row 3, tree 678, and its fruit was first described on Oct. 15, 1971 and the tree was marked as worthy of further observation. On Oct. 15, 1972, it was described again and at the time was given the selection number of NY 429. This selection was made by Dr. Robert D. Way who was the apple breeder at the time and is now Professor Emeritus. Propagation wood was taken from R3T678 to make new trees which were planted in May of 1975 and fruited for 11 years until the orchard was removed. Trees were also made and planted in May of 1983, fruiting from 1986 to the present time. Asexual reproduction was first performed by cleft grafting onto a seven year old seedling and by budding onto MM.106 rootstock in 1973 in Geneva, N.Y. Trees were also distributed to collaborators in the USA through the Fruit Testing Nursery Association NY (formerly named the New York Fruit Testing Association), Hedrick Hall, New York State Agricultural Experiment Station, Geneva. These collaborators assisted us in evaluating the merits of this selection under restricted nondistribution test agreements. NY 429 is being named and released as 'Fortune' and is the subject of this invention.

DESCRIPTION OF RELATED ART

'Fortune' is a hybrid of 'Empire' and a sport of 'Northern Spy'. The cross was made with the objective of combining desirable attributes from each parent and minimizing any negative characteristics that the parents might possess. In detailing the performance of 'Fortune' it is therefore necessary to compare its attributes with those of its parents. The parents of 'Fortune' are popular varieties in New York. In 1994 production of 'Empire' in New York State was 75 million pounds and that of 'Northern Spy' was 20 million pounds. Future production of 'Empire' is expected to expand, in New York and in other regions of the US, while that of 'Northern Spy' will decline because orchards of this variety are being removed and new replacement trees are not being planted (Stiles, 1992). 'Northern Spy' is an excellent processing variety, having received the highest rating for processing in comparison testing (Mohr and Adair, 1974). It has excellent flesh color for sauce and good flavor. It is consumed fresh and for pies, sauce, baking and salads. It has been used as a standard of quality in processing. However it has declined in commercial importance because the trees are slow to come into bearing and even after cropping starts, trees often bear good crops only every other year (i.e. biennially). Fruits are susceptible to bitter pit caused by calcium deficiency. Fruits are not attractive, being a pale, somewhat faded pinkish red. 'Empire' is primarily used for the fresh market. It has an attractive appearance and excellent flavor, but small size fruits are often a problem. It is used in processing, but is not rated highly for this purpose. 'Fortune' combines the desirable appearance of 'Empire' with much larger fruit size and processing quality of 'Northern Spy', without the production problems of 'Northern Spy'. Its tree structure is intermediate to that of its two parents. It offers growers and consumers a large attractive fruit that can be used fresh or for cooking. Processing tests were conducted by Cadbury Beverages and 'Fortune' was found to produce good apple sauce. It was rated as slow to oxidize (brown), juicy, good flavor and high Brix. On the basis of these tests Norris (1994) stated that NY 429 ('Fortune') had excellent processing characteristics.

Comparison to Parental Cultivars

A random sample of ten fruits of 'Fortune' were compared to those of 'Empire' and 'Northern Spy'. 'Schoharie Spy' could not be used for comparison because it is no longer in our collection, but 'Northern Spy' is a suitable replacement because it is identical to 'Schoharie Spy' except for having less color.

| Traits | 'Empire' | 'Northern Spy' | 'Fortune' |
|---|---|---|---|
| Diameter | 70–76 mm | 90–95 mm | 92–100 mm |
| Brix | 14.3 | 13.9 | 13.8 |
| Acid | .65 | .76 | .49 |
| Brix/Acid | 22 | 18 | 28 |
| Firmness (lbs) | 16.6 | 15.4 | 13.5 |
| Weight (g.) | 188 | 329 | 341 |

For the majority of traits examined, 'Fortune' is similar to 'Northern Spy'. Fruit size, weight, and Brix are equivalent or better than 'Northern Spy'. 'Fortune' has much lower acid than 'Northern Spy' which corresponds to a high Brix/acid ratio. A high Brix/acid ratio is desired by many processors and retailers because of a belief that it corresponds to higher quality. Fruit firmness as measured by a penetrometer was lower in 'Fortune' than in both parents. This lower firmness is not desirable, but firmness is a trait that is highly influenced by many environmental factors so that it may be manipulated culturally, and it can vary from year to year. Firmness tests in 1994 showed 'Fortune' (17 lbs) to be intermediate between 'Empire' (15.9 lbs) and 'Northern Spy' (18.8). Although we did not have a quantitative measurement of the tendency to bruise, subjective evaluations indicated that 'Fortune' was equivalent or better than its parents.

DESCRIPTION OF THE INVENTION

This invention relates to a new and distinctive cultivar of apple, named 'Fortune', which we discovered in a test planting belonging to the New York State Agricultural Experiment station, Cornell University, Geneva, Ontario County, N.Y. this discovery is a product of an apple breeding research program of the New York State Agricultural Experiment Station.

Pollination: 'Fortune' was used in controlled hybridizations as a pollen parent and a seed parent and good fruit set was obtained indicating that it is diploid and that pollen is viable. Reports from other collaborators researchers and growers operating under nondistribution test agreements have indicated that fruit set is not a problem.

DETAILED PLANT DESCRIPTION

Figure 1:
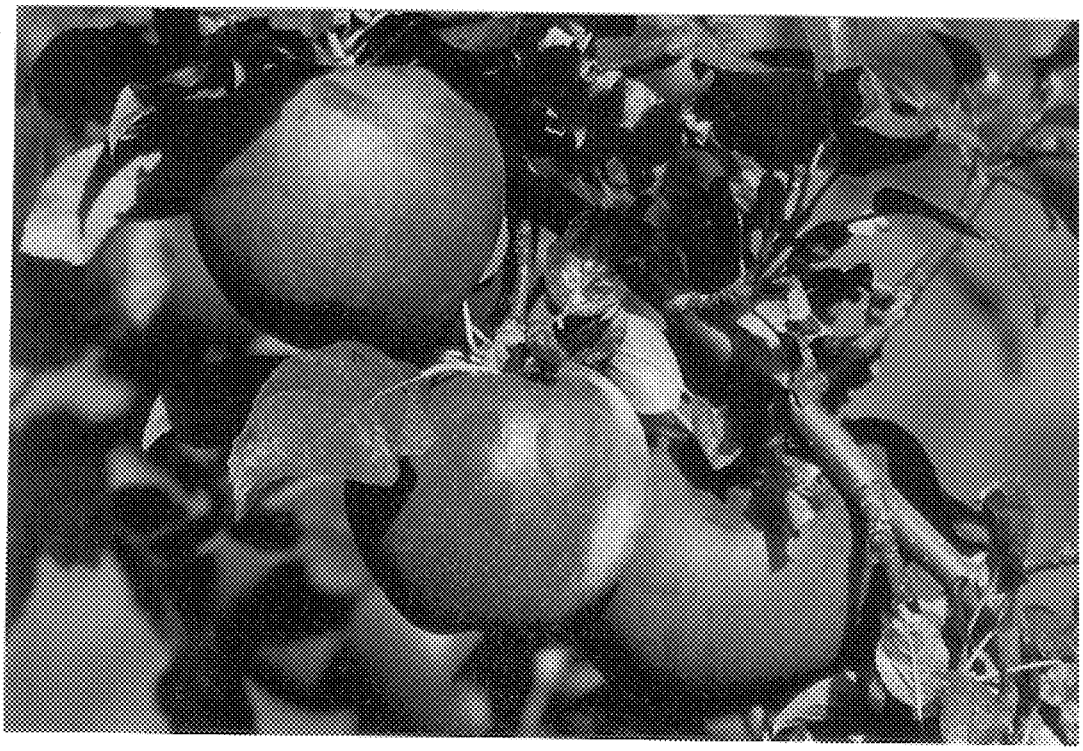
FIG. 1. Fruit of 'Fortune' growing on the tree.
Figure 2:
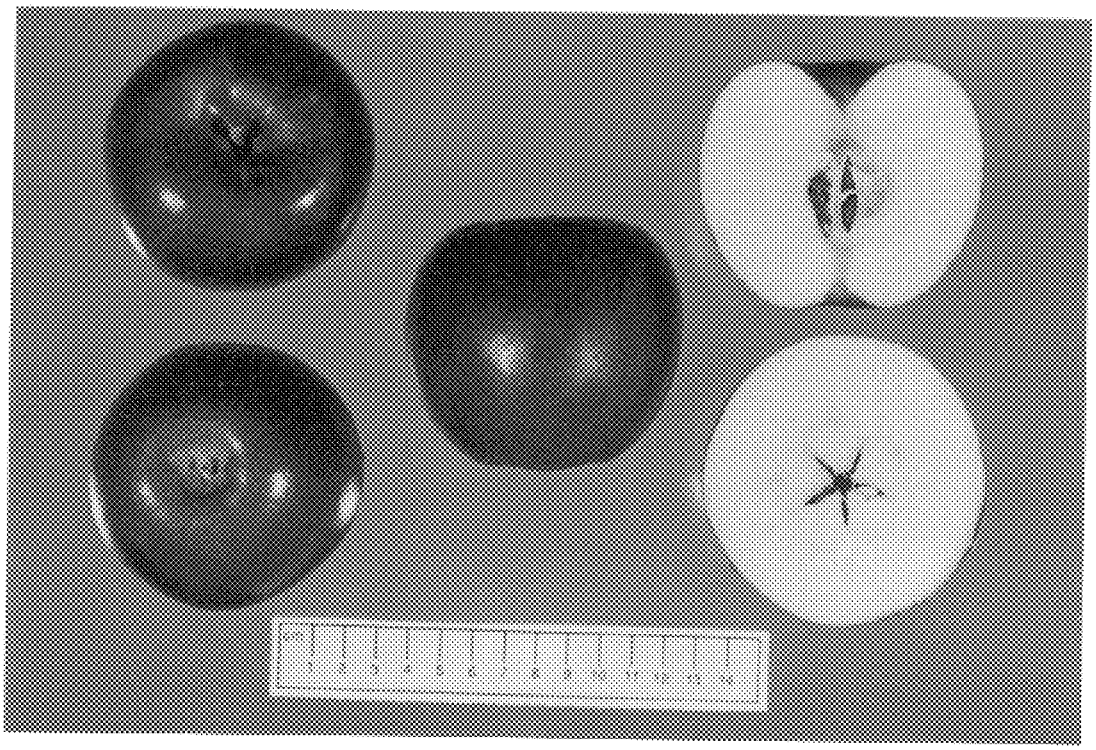
FIG. 2. Fruit of 'Fortune'.
Figure 3:
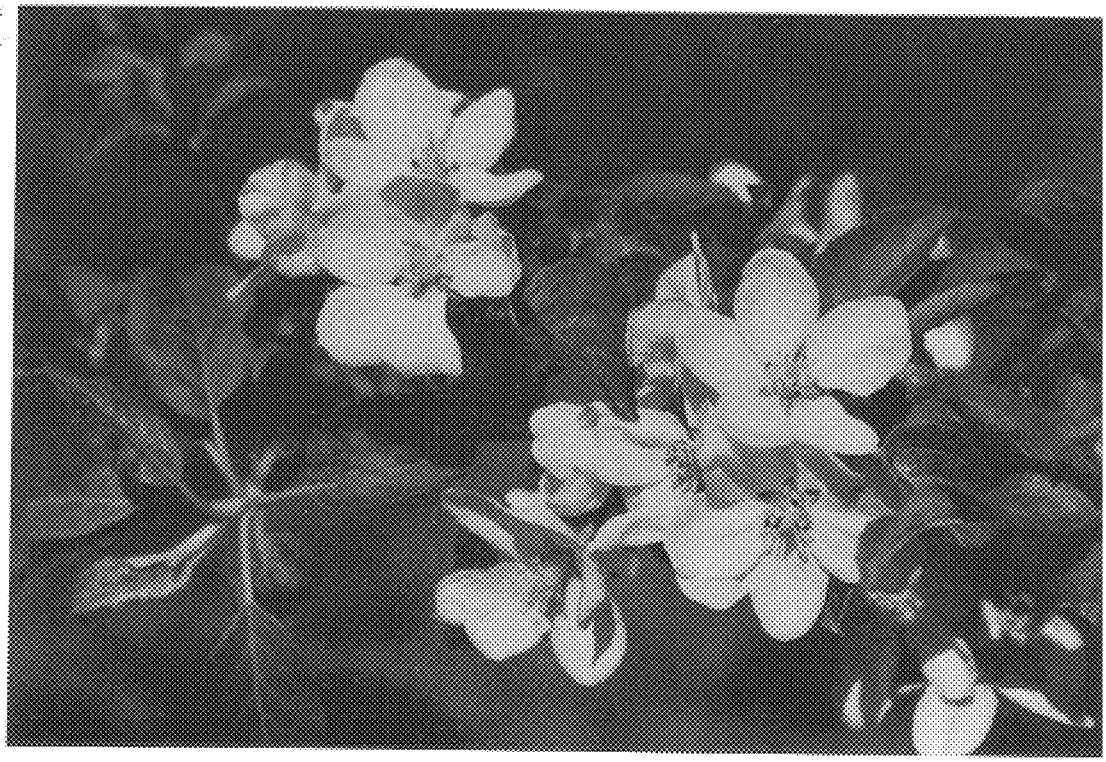
FIG. 3. Flower of 'Fortune' Growing on the tree.
Figure 4:
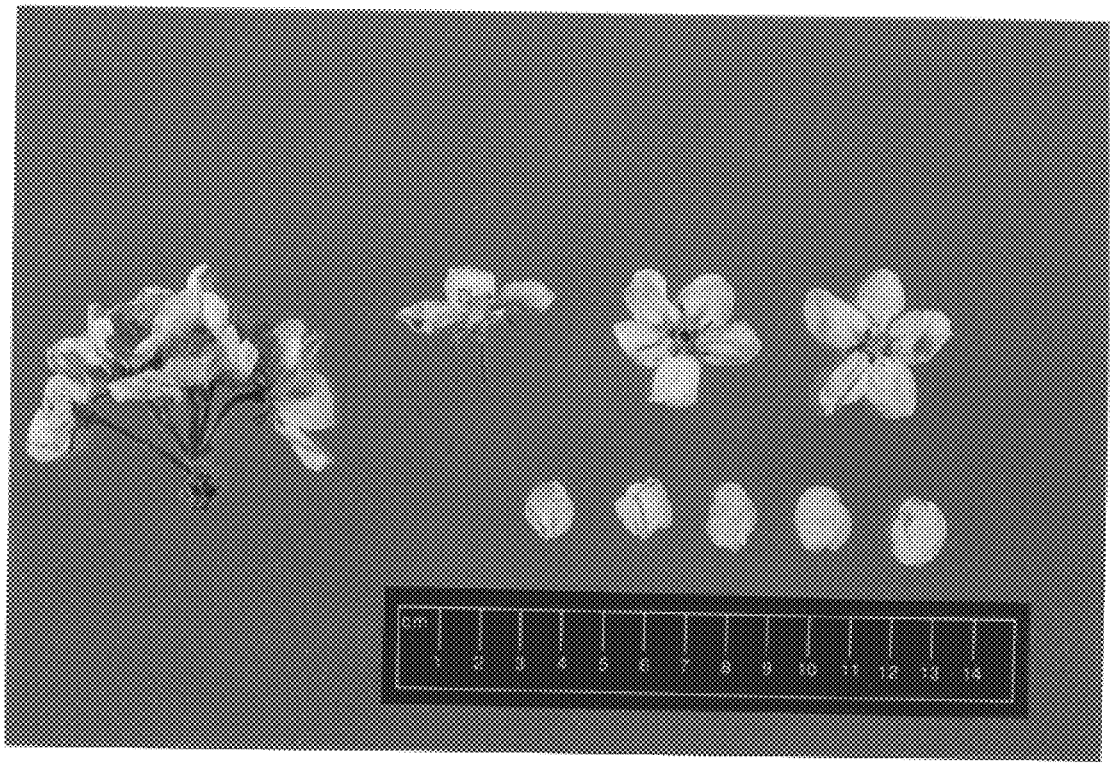
FIG. 4. Flowers of 'Fortune'.
Figure 5:
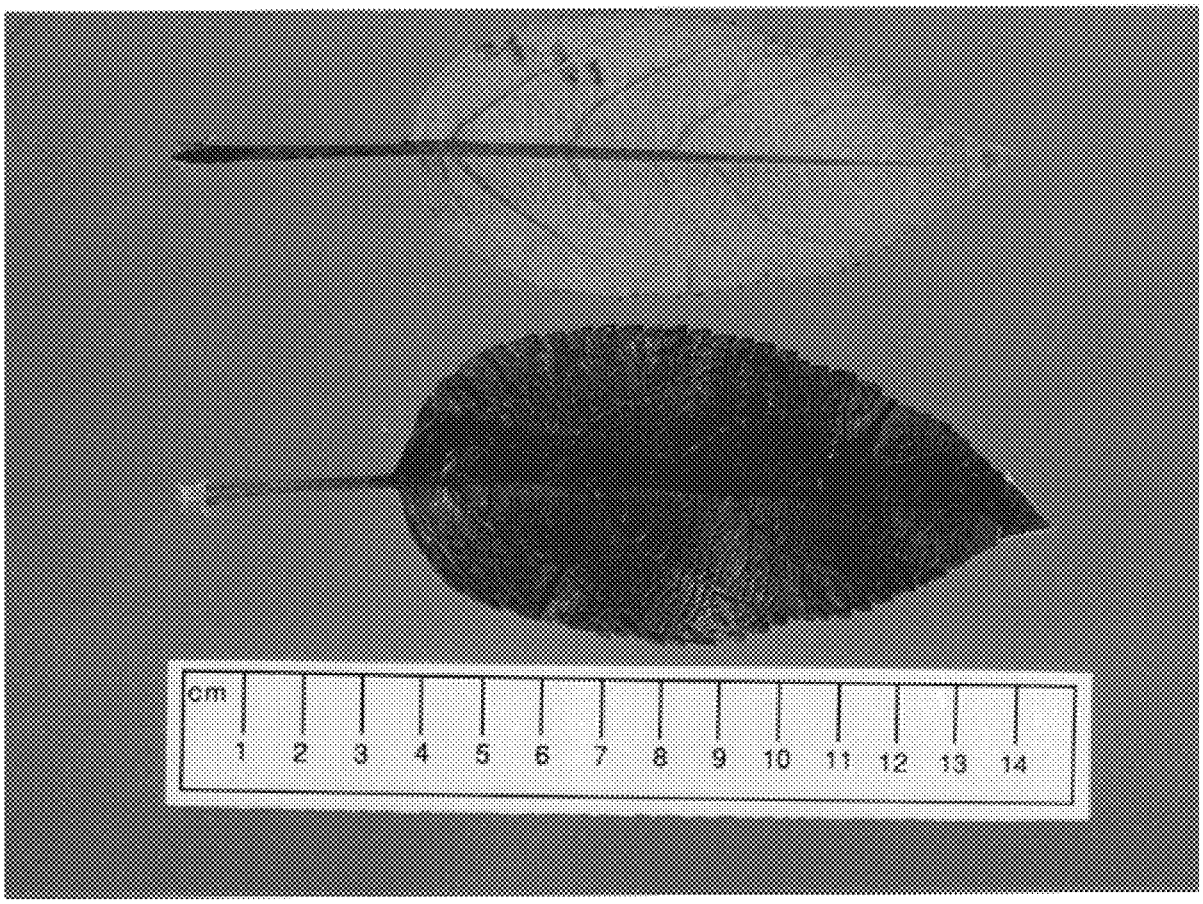
FIG. 5. Leaves of 'Fortune'.

Accompanying FIGS. 1-6 depict flowers, leaves, fruits (dissected and whole), fruits on the tree, and the intact tree. The numerical color designations employed in this patent disclosure are those of The R. H.S. Colour Chart (1966):

Flowers: Flowers (FIG. 4) are white tinged with Magenta Rose Red Group 56D when fully open. The corolla approximates 38 mm at anthesis, with the petals 10 mm×15 mm (FIG. 4). The flowers are single and have no unusual features that distinguish them from other apple cultivars. They are symmetrically typical of *Malus X domestica* flowers. Exact dates of bloom are difficult to specify due to environmental effects and crop load but the bloom of 'Fortune' has been found to coincide with that of 'Empire' and 'McIntosh.' The date of 90% flowers opening at Geneva, N.Y. in 1998 was May 3, but in 1997, it was May 12.

Fruit: 'Fortune' fruits (FIG. 1 and FIG. 2) are oblate conic in shape, ribbed and slightly irregular. They are large (88 mm long×94 mm wide). Fruits are Greyed-Purple Group 187C with stripes Greyed-Purple Group 187B. The undercolor or background color is Yellow-Green Group 154A at harvest and lightens to 154C with delayed harvest or after storage. There is a range in per cent fruit coloration, with 90% average, but 70 to 100% coloration is the range observed at harvest. Color expression is greatly influenced by cultural manipulations that provide adequate light penetration to the fruits. Stripes are 1.0 to 1.5 mm wide and in length they vary from 0.5 mm to covering the entire length of the fruit. The portion of the fruit that might present stripes is 30 to 40% of the total coloration, with the remaining coloration blush. Stripes are over the blush and are sometimes undistinguishable from the blush. The over color of the fruit does not change with storage, but the subcolor or ground color may change from Yellow-Green Group 154A to Yellow Green Group 154C with maturity or storage indicating a lightening of the ground color. The fruits are considered very attractive and very similar to 'Empire' in coloration. The skin is thick, tough, nearly smooth, glossy under a slight bloom and dots are numerous, small and sunken. The fruit stems range from 11 mm to 23 mm in length and typically are 3.8 mm thick. The stem color is Yellow-Green Group 154B with 25% of its surface Red Group 46A. The stem cavity is deep, medium broad, green and furrowed. The basin is deep, medium broad, abrupt and furrowed. The calyx is closed and small, lobes are short and broad. The calyx tube is long, narrow, and conical, stamens are medium. Core-lines are clasping. The core is open and large. Moldy core is observed sporadically. Carpels are tufted. Seeds are medium in length and width, light brown (Brown Group 200C), 10 per fruit.

Flesh is light yellow in color (Yellow Group 11D), but at early maturity dates it may have a greenish tinge. The texture is firm, crisp, and course. Quality is very good, with flavor characterized as subacid, sprightly and juicy. Some watercore has been observed.

'Fortune' is susceptible to russetting of the fruit surface if there is frost during fruit development, or if environmental conditions are such as to slow drying of spray materials. Russetting does not occur frequently and only 5% of the fruits are affected with russetting in years when russetting occurs.

*Maturity season.*—Ripens with 'Empire' or slightly after 'Empire'. Harvest indices need to be developed because starch iodine testing may not be the best indicator of maturity.

*Harvest.*—Harvest evaluations at Geneva, N.Y. indicate that the harvest period coincides with that of 'Empire.' The date will vary as to season and crop load, but frequently occurs during the first and second weeks of October in Geneva, N.Y. These observations spanned over 10 years of comparison with 'Empire.' There is some variability in ripening as occurs with most apple cultivars, but 'Fortune' is a cultivar that does not require a series of multiple harvests. Fruits can be harvested at a single date or two harvests can be conducted. Fruits are not usually subject to pre-harvest drop, but storage on the tree is not recommended because any apples that are left on a tree will start deteriorate in quality.

*Keeping quality.*—'Fortune' is similar to its parents in keeping quality in storage.

Figure 6:
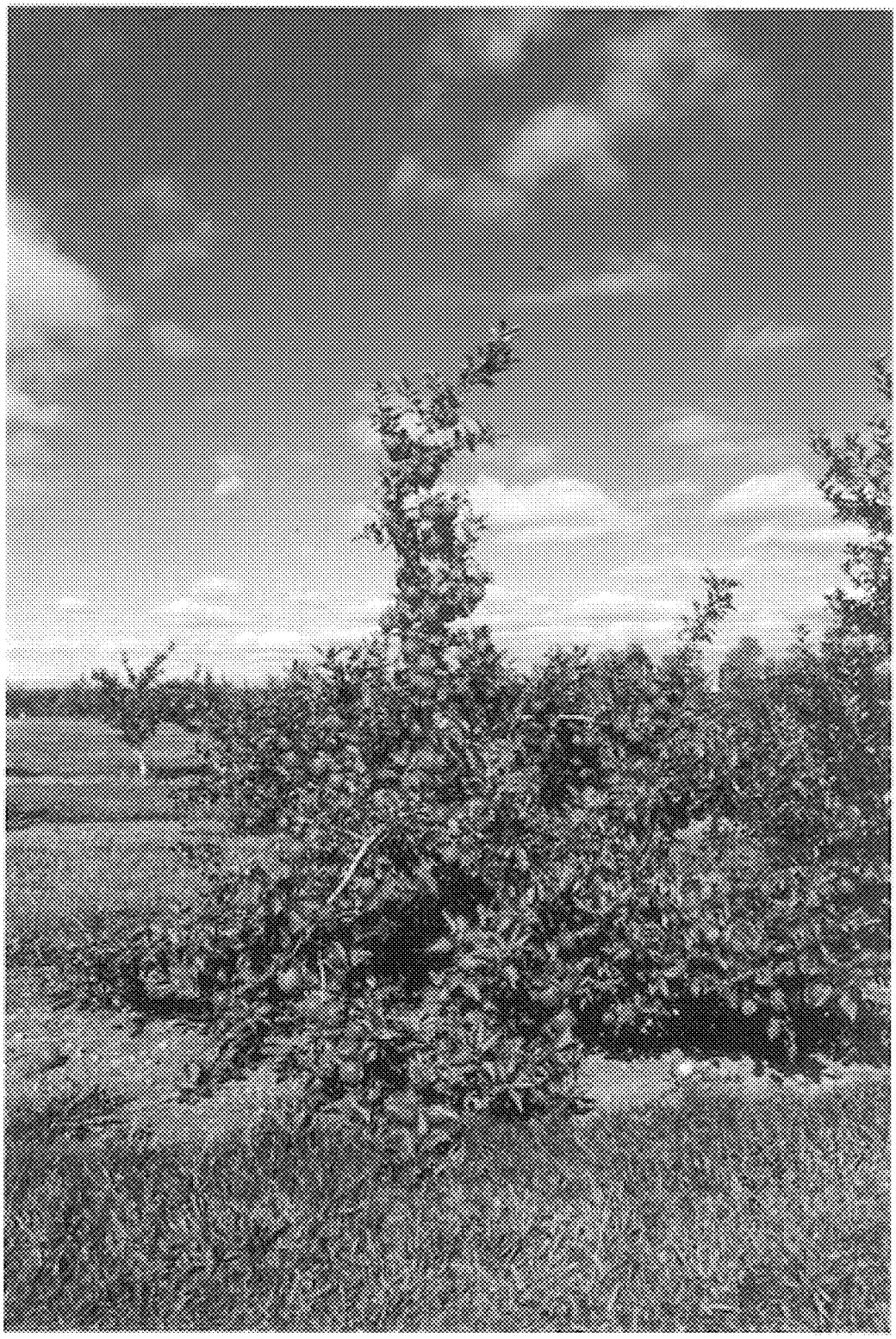
FIG. 6. 'Fortune' tree.

Tree: Trees are vigorous and upright (FIG. 6). The use of dwarfing rootstocks is recommended to control vigor and allow an open canopy for light penetration to enhance quality and coloring of fruits. Many cooperators (researchers and growers operating under nondistribution test agreements) have reported favorable performance on Malling 9 rootstocks. Branch angle varies from 5 to 80 degrees due to the training system used and properly trained and thinned branches should not be subject to breakage. 'Fortune' bears readily on spurs. 'Fortune' has been treated on dwarfing stocks M.26 and M.9, and while it is vigorous, it would be suitable for high density plantings. If dwarfing rootstocks are used, as with any tree on dwarfing rootstocks, supplemental support such as a wire trellis is recommended. For older trees, the tree would be regarded as more spreading than upright. Younger non-bearing trees are very upright, but training and crop load modifies the form to a more spreading habit. The tree would regarded as having a predominantly spur-bearing habit. The tree would be regarded as having the capacity to bear fruits in sufficient number and size as to break branches without supplemental support. It is important to note that almost all apple cultivars have the capacity to bear fruits in sufficient number and size to break branches without supplemental support. Proper tree training, pruning, and thinning of fruits to prevent overcropping are required to minimize the possiblity of limb breakage. As indicated above, trees on dwarfing rootstocks require some type of wire trellis or support system. 'Fortune' descriptions are based on performance on MM.106, M.26 and M.9 rootstocks. These are the rootstocks used commercially in New York State and in other apple growing regions. 'Fortune' has not been grown on its own roots except as a seedling tree in the years 1964 to 1975, and detailed observations were not made on seedling form. The seedling tree is no longer in existence.

Leaves: Leaves of 'Fortune' (FIG. 5) are large, up to 105×70 mm. Spur leaves are quite narrow, pointed, thick, rather rugose, and dark green. The upper leaf surfaces are shiny, with lower leaf surfaces dull and quite tomentose. Serrations are medium to large and pointed. The petiole is stout, 35 mm long and pubescent. Stipules are fairly persistent, 10 mm long and narrow. Leaf upper surface and stipules are Green Group 137A. The green of the leaf lower surface is Grey-Green Group 195C. The petiole is Red Group 53A.

*Adaptation to growing regions.*—'Fortune' appear to be adapted to a wide range of growing conditions. Favorable performance ratings have been given by cooperators (researchers and growers operating under nondistribution test agreements) throughout New York, in New England, and even in warm regions of the Pacific Northwest where growers reported that it was able to take the heat and still produce fruit of good quality.

*Resistance/susceptibility.*—'Fortune' has average susceptibility to most apple diseases and pests. It does not possess specific genes for resistance to scab. It has been reported to be susceptible to the bacterium *Erwinia amylovora*, the causal agent of fire blight, but infection is limited to one-year wood.

Usefulness

'Fortune' is an excellent dual use variety, because it is suitable for fresh market and processing. It provides growers and consumers with a large attractive fruit with good flavor and texture that can be eaten fresh or used in baking or salads. For growers it offers a mid-season variety with 'Northern Spy' quality that is productive and less prone to production problems than 'Northern Spy'.

What is claimed:

1. A new and distinct apple tree cultivar as herein described and illustrated.

* * * * *